US008847740B2

(12) United States Patent
Kiani et al.

(10) Patent No.: US 8,847,740 B2
(45) Date of Patent: Sep. 30, 2014

(54) ALARM SUSPEND SYSTEM

(71) Applicant: Masimo Corporation, Irvine, CA (US)

(72) Inventors: Massi Joe E. Kiani, Laguna Niguel, CA (US); Steve L. Cebada, Mission Viejo, CA (US); Gregory A. Olsen, Trabuco Canyon, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 14/036,496

(22) Filed: Sep. 25, 2013

(65) Prior Publication Data

US 2014/0125478 A1 May 8, 2014

Related U.S. Application Data

(63) Continuation of application No. 13/476,725, filed on May 21, 2012, now Pat. No. 8,547,209, which is a continuation of application No. 12/510,982, filed on Jul. 28, 2009, now Pat. No. 8,203,438.

(60) Provisional application No. 61/084,615, filed on Jul. 29, 2008.

(51) Int. Cl.
G08B 5/22 (2006.01)
(52) U.S. Cl.
USPC .............. 340/286.07; 340/539.12; 340/573.1; 600/322; 600/323; 600/324; 607/28
(58) Field of Classification Search
USPC ............ 340/517, 573.1, 539.12, 286.07, 527; 128/905; 600/310, 316, 322–324, 336, 600/344, 507, 301, 320; 607/28
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| D361,840 | S | 8/1995 | Savage et al. |
| D362,063 | S | 9/1995 | Savage et al. |

(Continued)

FOREIGN PATENT DOCUMENTS

WO WO 2005/087097 A 9/2005

*Primary Examiner* — Brent Swarthout
(74) *Attorney, Agent, or Firm* — Knobbe, Martens, Olson & Bear, LLP

(57) ABSTRACT

An alarm suspend system utilizes an alarm trigger responsive to physiological parameters and corresponding limits on those parameters. The parameters are associated with both fast and slow treatment times corresponding to length of time it takes for a person to respond to medical treatment for out-of-limit parameter measurements. Audible and visual alarms respond to the alarm trigger. An alarm silence button is pressed to silence the audible alarm for a predetermined suspend time. The audible alarm is activated after the suspend time has lapsed. Longer suspend times are associated with slow treatment parameters and shorter suspend times are associated with fast treatment parameters.

20 Claims, 5 Drawing Sheets

(56) References Cited

U.S. PATENT DOCUMENTS

| | | |
|---|---|---|
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |

(56) References Cited

U.S. PATENT DOCUMENTS

| | | |
|---|---|---|
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,570,152 B2 | 8/2009 | Smith et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,160,671 B2 | 4/2012 | Kamath et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |

(56) References Cited

U.S. PATENT DOCUMENTS

| | | |
|---|---|---|
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 2002/0161291 A1 | 10/2002 | Kianl et al. |
| 2003/0137243 A1 | 7/2003 | Costello |
| 2003/0191358 A1* | 10/2003 | MacKin et al. ................. 600/22 |
| 2008/0103375 A1 | 5/2008 | Kiani |
| 2008/0244425 A1 | 10/2008 | Kikin-Gil et al. |
| 2010/0331656 A1 | 12/2010 | Mensinger et al. |
| 2012/0105233 A1* | 5/2012 | Bobey et al. ............... 340/573.4 |
| 2012/0303085 A1* | 11/2012 | Vitense et al. ................. 607/28 |

* cited by examiner

ALARM SUSPEND SYSTEM

CROSS-REFERENCE TO RELATED APPLICATIONS

This application is a continuation of U.S. patent application Ser. No. 13/476,725, filed May 21, 2012, now U.S. Pat. No. 8,547,209, and titled "Alarm Suspend System," which is a continuation of U.S. patent application Ser. No. 12/510,982 filed Jul. 28, 2009 now U.S. Pat. No. 8,203,438, and titled "Alarm Suspend System," which claims priority benefit under 35 U.S.C. §119(e) to U.S. Provisional Patent Application Ser. No. 61/084,615, filed Jul. 29, 2008, titled "Alarm Management System." All of the above referenced applications are hereby incorporated by reference in their entireties herein.

BACKGROUND

Pulse oximetry for measuring constituents of circulating blood has achieved acceptance in a wide variety of medical applications, including surgical wards, intensive care and neonatal units, general wards, home care, physical training, and virtually all types of monitoring scenarios. A pulse oximeter generally includes a two-wavelength optical sensor applied to a patient, a monitor for processing sensor signals and displaying results and a patient cable electrically interconnecting the sensor and the monitor. The monitor typically provides a numerical readout of physiological parameters such as oxygen saturation ($SpO_2$) and pulse rate (PR). Advanced physiological monitors utilize multiple wavelength sensors and enhanced measurement capabilities to provide readouts of additional parameters, such as carboxyhemoglobin (HbCO), methemoglobin (HbMet) and total hemoglobin (Hbt).

Pulse oximeters capable of reading through motion induced noise are disclosed in at least U.S. Pat. Nos. 6,770,028, 6,658,276, 6,650,917, 6,157,850, 6,002,952, 5,769,785 and 5,758,644; low noise pulse oximetry sensors are disclosed in at least U.S. Pat. Nos. 6,088,607 and 5,782,757; all of which are assigned to Masimo Corporation, Irvine, Calif. ("Masimo") and are incorporated by reference herein.

Physiological monitors and corresponding multiple wavelength optical sensors are described in at least U.S. patent application Ser. No. 11/367,013, filed Mar. 1, 2006 and titled Multiple Wavelength Sensor Emitters and U.S. patent application Ser. No. 11/366,208, filed Mar. 1, 2006 and titled Noninvasive Multi-Parameter Patient Monitor, both assigned to Masimo Laboratories, Irvine, Calif. (Masimo Labs) and both incorporated by reference herein.

Further, physiological monitoring systems that include low noise optical sensors and pulse oximetry monitors, such as any of LNOP® adhesive or reusable sensors, SofTouch™ sensors, Hi-Fi Trauma™ or Blue™ sensors; and any of Radical®, SatShare™, Rad-9™, Rad-5™, Rad-5v™ or PPO+™ Masimo SET® pulse oximeters, are all available from Masimo. Physiological monitoring systems including multiple wavelength sensors and corresponding noninvasive blood parameter monitors, such as Rainbow™ adhesive and reusable sensors and RAD-57™ and Radical-7™ monitors for measuring $SpO_2$, pulse rate (PR), perfusion index (PI), pleth variability index (PVI), signal quality, HbCO and HbMet among other parameters are also available from Masimo.

SUMMARY OF THE INVENTION

Monitor alarms are triggered by out-of-limit parameters and system failures, the latter including monitor or sensor failures or improper sensor placement, to name a few. Alarms can be visual, audible or both. Alarms can also have different levels of priority, which are reflected in the type of visual and audible alarms. In an embodiment, parameters exceeding limits such as low $SpO_2$, high HbCO, high HbMet and low and high BPM trigger high priority alarms. System failures due to sensor off, no sensor or defective sensor also trigger high priority alarms. Parameters exceeding limits such as high $SpO_2$, low and high PI, low and high PVI, for example, trigger medium priority alarms. Parameters exceeding limits such as low HbCO and low HbMet along with a system low battery indication are examples of low priority alarms.

An audible alarm may be temporarily suspended by pressing an alarm silence button so as to prevent unnecessary disturbance to the patient and distraction of the caregiver. During alarm suspension, visual alarms remain active. If an alarm condition persists after a predetermined alarm suspend period, the audible alarm resumes. The alarm suspend period is typically long enough to give a caregiver sufficient time to intervene with appropriate patient treatment yet short enough to ensure that patient health is not endangered if intervention is ineffective. For conventional pulse oximetry, an alarm suspend may be, for example, a maximum of 120 seconds.

Alarm suspension on advanced blood parameter monitors is problematic. With conventional pulse oximetry, treatment for abnormal parameter measurements can be quickly applied and a patient response is typically fast. For example, a treatment for low oxygen saturation is the application of an oxygen mask or an increase in oxygen flow. By contrast, the duration of treatment for parameters measured by advanced monitors is highly dependent on the alarm-triggering parameter. For example, the treatment for high methemoglobin is the injection of methylene blue, and the patient response to such an injection is slow. When patient treatment time exceeds the maximum alarm suspend period, an audible alarm will constantly reactivate. Thus, a single alarm suspend duration for all parameters is inadequate to cope with the many different types of parameters measured by advanced monitors.

One aspect of an alarm suspend system for silencing the alarms is an alarm trigger responsive to any of various parameters and predetermined limits corresponding to the parameters, where the parameters are partitioned according to treatment time, i.e. the relative length of time it takes for a person to respond to medical treatment for a parameter measurement outside of the predetermined limits. An audible alarm is responsive to the alarm trigger. An alarm silence button is actuated so as to suspend the audible alarm. A timer tracks the duration of the suspended alarm and is initiated by actuation of an alarm silence button. The timer retriggers the audible alarm after the timed duration has lapsed/expired. In an embodiment, a long duration suspend time is associated with slow treatment parameters and a short duration suspend time is associated with fast treatment parameters. Fast treatment parameters may include, for example, parameters relating to normal blood hemoglobin constituents and slow treatment parameters may include parameters relating to abnormal blood hemoglobin constituents.

In various embodiments, a short duration suspend time is less than or equal to about two minutes and a long duration suspended time is greater than about two minutes. A default duration associated with the fast treatment parameters is about two minutes and a default duration associated with the slow treatment parameters is about fifteen minutes. The alarm suspend system may also have an alarm suspend override responsive to a predetermined unit change in the parameter triggering a suspended alarm. The override results in reactivation of the suspended alarm. A physiological monitor having an alarm suspend system may also have a pop-up window that appears on the monitor display in response to actuation of the silence button, where the pop-up window presents a choice of alarm suspend durations.

Another aspect of an alarm suspend system is a partition of measured parameters into at least a first group and a second group. An audible alarm is triggered if at least one parameter is outside of predetermined limits. The audible alarm is suspended in response to a silence request. A first duration is associated with the first group and a second duration is associated with the second group. The audible alarm is reactivated after at least one of the first duration and the second duration. The first duration may be set so as to generally correspond to a first range of treatment times for the first group of parameters. Likewise, the second duration may be set so as to generally correspond to a second range of treatment times for the second group of parameters, where the first range of treatment times and the second range of treatment times are non-overlapping.

In various embodiments, suspended audible alarms are overridden if the triggering parameter has greater than a predetermined unit change before the suspended alarm expires according to either the first duration or the second duration. The first and second groups are defined in relation to normal hemoglobin measurements abnormal hemoglobin measurements, respectively. The first duration is set to be less than or equal to two minutes and the second duration is set to be greater than two minutes, with default durations of about two minutes corresponding to the first group and about fifteen minutes corresponding to the second group. In an embodiment, a pop-up window for a monitor display is constructed and the first duration and the second duration are selected from a range of durations presented within the pop-up window.

A further aspect of an alarm suspend system deactivates an audible alarm for one of a short duration and a long duration according to the alarm-triggering parameter. A first group of parameters is associated with the short duration and a second group of parameters is associated with the long duration. The first group and the second group are partitioned according to a fast treatment time and a short treatment time associated with the parameters. An override reactivates the audible alarm if the trigger parameter changes more than a predetermine amount during the corresponding duration. In various embodiments, the first group comprises parameters related to the measurement of normal hemoglobin and the second group comprises parameters related to the measurement of abnormal hemoglobin. The long duration is greater than about 120 seconds and the short duration is less than or equal to about 120 seconds. A pop-up window for the display allows selection of the long duration and the short duration in response to the silence button.

DETAILED DESCRIPTION

Figure 1:
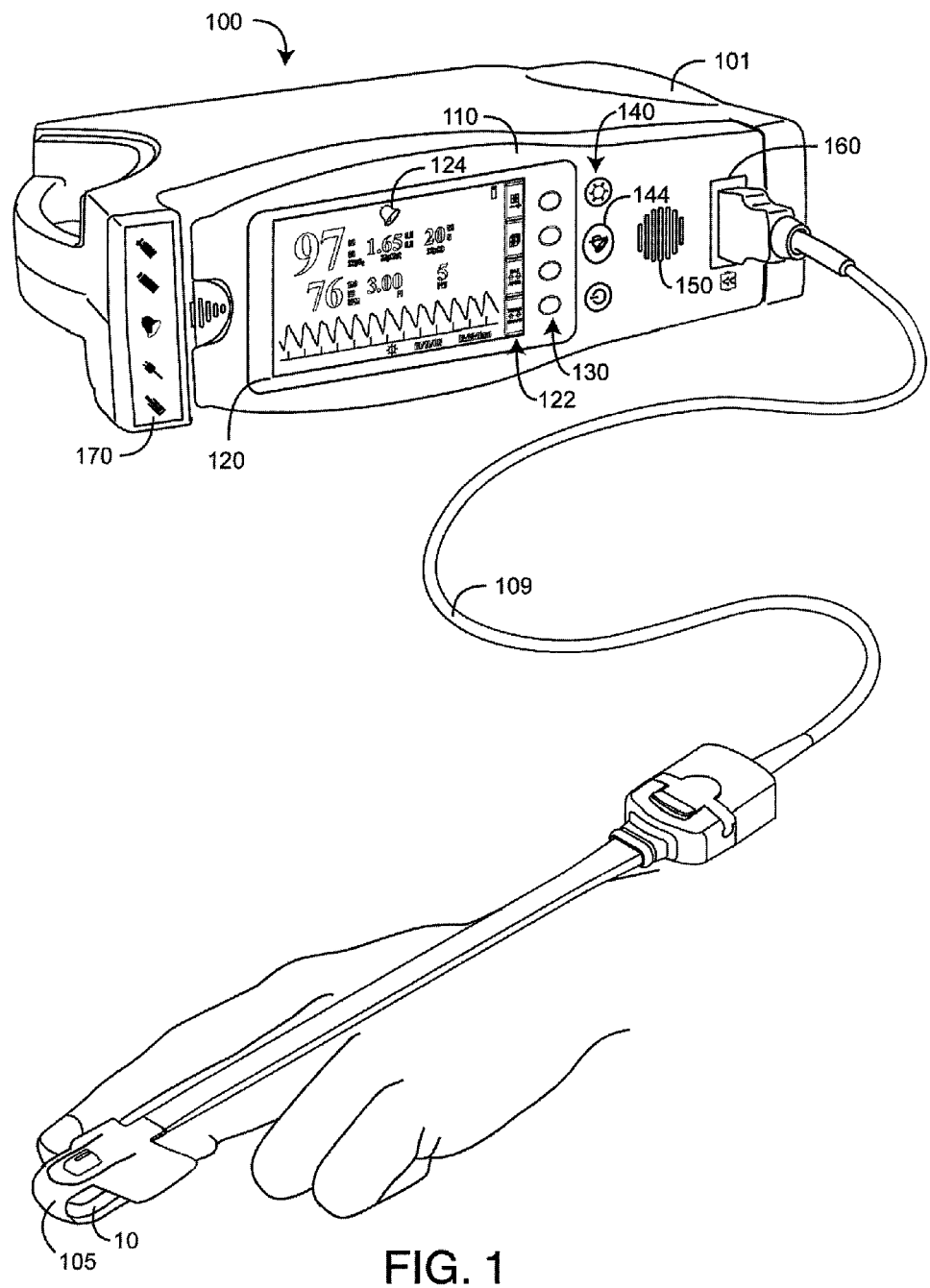
FIG. 1 is a perspective view of a physiological measurement system utilizing an alarm suspend system.

FIG. 1 illustrates a physiological measurement system 100 that utilizes an alarm suspend system. The physiological measurement system 100 has a noninvasive sensor 105 attached to a tissue site 10, a physiological monitor 101, and an interface cable 109 interconnecting the monitor 101 and the sensor 105. The physiological measurement system 100 may incorporate pulse oximetry in addition to advanced features, such as a multiple wavelength sensor and advanced processes for determining physiological parameters other than or in addition to those of pulse oximetry, such as carboxyhemoglobin, methemoglobin and total hemoglobin, as a few examples.

The monitor 101 has a front panel 110 providing a display 120, touch keys 130, controls 140, a speaker 150, a sensor port 160 and status indicators 170. The display 120 shows parameter readouts, limits and waveforms among other items. The display 120 also has touch key icons 122 that indicate touch key 130 functions. The speaker 150 provides an audible alarm in response to physiological measurements that violate preset conditions, such as an out-of-limit parameter, as well as system failures, such as a low battery condition. The controls 140 include an alarm silence button 144 that is pressed to temporarily suspend out-of-limit parameter alarms and system alarms, such as low battery. The display 120 provides visual alarms, which include a bell-shaped alarm status indicator 124 that illuminates during an alarm condition and parameter readouts 210 and limits 220 that flash when parameters are out-of-limit. Status indicators 170 also provide visual alarms. When there are multiple alarm conditions, the parameter displays 202 indicate parameters with the highest alarm priority. Touch keys 130 and corresponding icons 122 include an alarm menu access button for setting alarm conditions, such as high or low alarm limits for $SpO_2$, HbCO, HbMet, PR and PI. The alarm silence button 144 is pressed to temporarily suspend audible alarms. Advantageously, an alarm suspend system provides a parameter-dependent variation in the alarm suspend duration, as described below, utilizing a common silence button or other suspend initiator.

Figure 2:
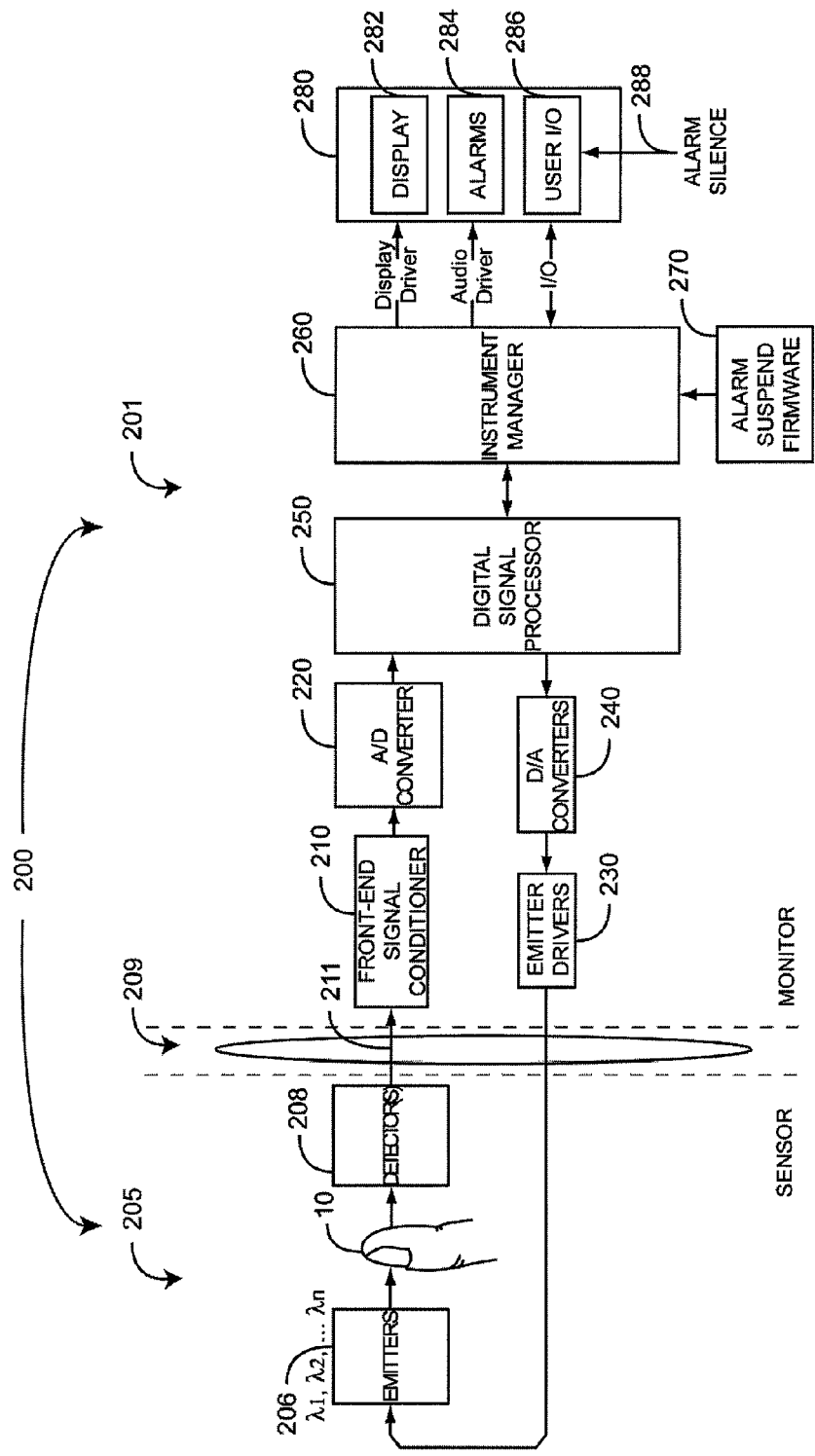
FIG. 2 is a detailed block diagram of a physiological measurement system utilizing an alarm suspend system.

FIG. 2 illustrates a physiological measurement system 200 including a physiological monitor 201, a sensor 205 and an interface cable 209. The sensor 205 is attached to a tissue site, such as a finger 10, and includes a plurality of emitters 206 irradiating the tissue site 10 with multiple wavelengths of light. The sensor 205 also includes one or more detectors 208 capable of detecting the light after attenuation by the tissue site 10. The sensor 205 transmits optical radiation at wavelengths other than or including the red and infrared wavelengths utilized in pulse oximeters. The monitor 201 inputs a corresponding sensor signal 211 and determines the relative concentrations of blood constituents other than or in addition to the "normal" blood hemoglobin constituents $HbO_2$ and Hb, including "abnormal" blood hemoglobin constituents HbCO, HbMet and blood related parameters such as fractional oxygen saturation, total hemoglobin and blood glucose to name a few.

As shown in FIG. 2, the monitor 201 has a front-end signal conditioner 210, an A/D converter 220, emitter drivers 230, D/A converters 240 and a digital signal processor ("DSP") 250. In general, the emitter drivers 230 convert digital control signals, via the D/A converters 240, into analog drive signals capable of driving the sensor emitters 206. The front-end signal conditioner 210 converts, via the A/D converter 220, composite analog intensity signal(s) from light sensitive detector(s) 208 into digital data input to the DSP 250. The emitter drivers 230 and front-end signal conditioner 210 communicate with the sensor 205 via the interface cable 209.

Also shown in FIG. 2, the monitor 201 has an instrument manager 260 and a user interface 280. The user interface 280 includes one or more displays 282, alarms 284 and user input/output (I/O) 286. The instrument manager 260 communicates with the DSP 250 to receive parameter data and to present that data on the display 282. The instrument manager 260 may also store and display historical or trending data related to one or more of the measured parameters or combinations of the measured parameters. The instrument manager 260 also controls audible and visual alarms and indicators 284. The instrument manager 260 responds to user-actuated keys and communicates with external devices via various I/O ports 286. Further, the instrument manager 260 executes alarm suspend firmware 270 so as to respond to an alarm silence button press 288, as described in detail with respect to FIGS. 3-4.

Figure 3:
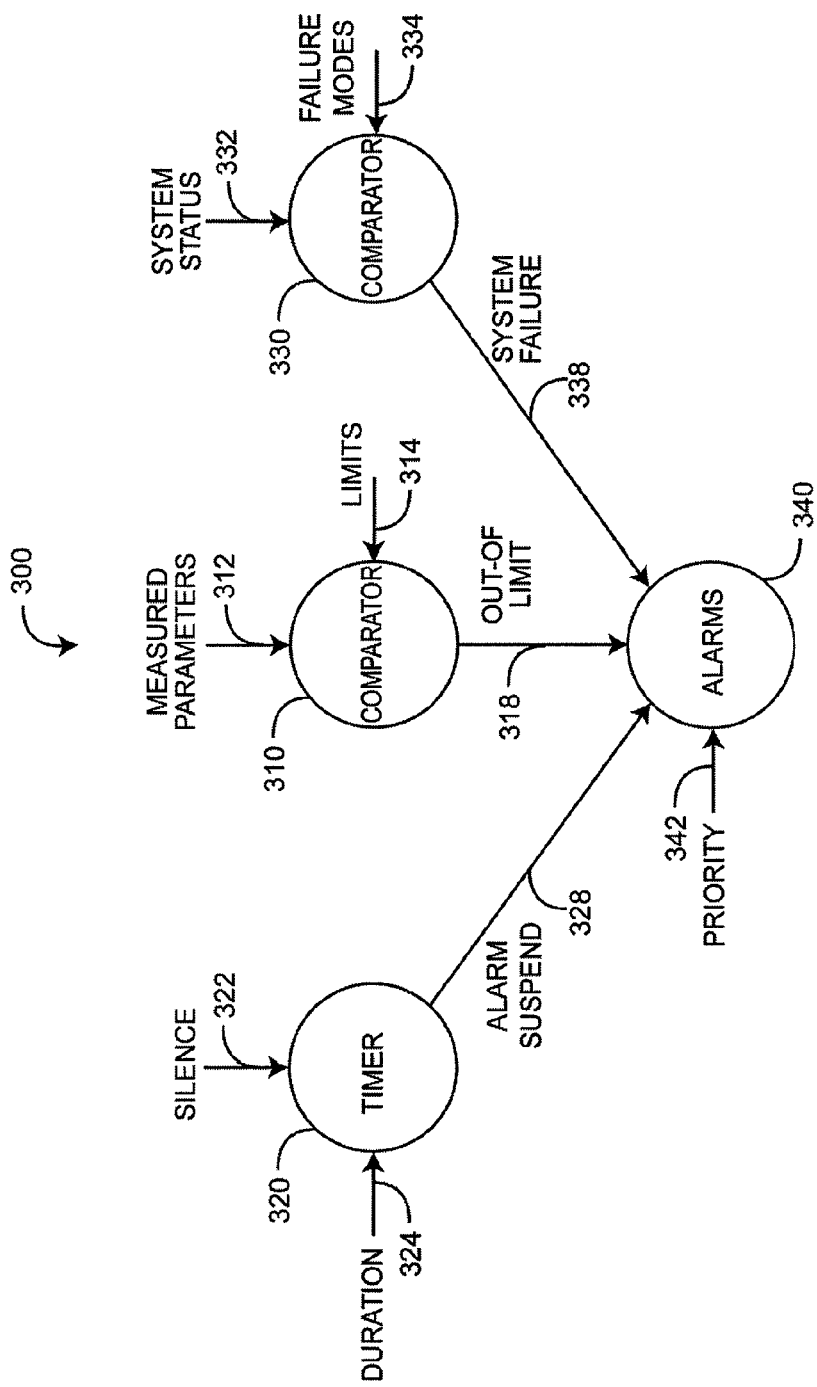
FIG. 3 is a flow diagram of an alarm suspend system embodiment.

FIG. 3 generally illustrates an alarm suspend system 300. Alarm triggers include system failures 338 and out-of-limit parameters 318. Triggered alarms 340 may be audible, visual or both, and may vary according to priority 342. Audible alarms may be generated by a monitor front-panel-mounted speaker 150 (FIG. 1) and may vary in loudness, pitch and sound pattern. Visual alarms may include parameter labels, parameter numerics, symbols and status lights, which can flash and vary in color.

As shown in FIG. 3, measured parameters 312 are compared 310 to default or user-specified limits 314. An out-of-limit condition 318 triggers an alarm 340. An alarm suspend 328 is user-initiated by a silence request 322. This may be a press of a silence button 144 (FIG. 1) on a monitor front panel 110 (FIG. 1). In an embodiment, the alarm suspend 328 silences audible alarms and modifies the display of visual alarms. The alarm suspend 328 is based on a timer 320, which ends the alarm suspend 328 after a predetermined duration 324. The duration 324 may be a function of the out-of-limit parameter 312. In an advantageous embodiment, the duration 324 relates to, or is a function of, the treatment time for the alarm-triggering parameter so as to avoid nuisance alarms while maintaining alarm integrity.

Figure 4:
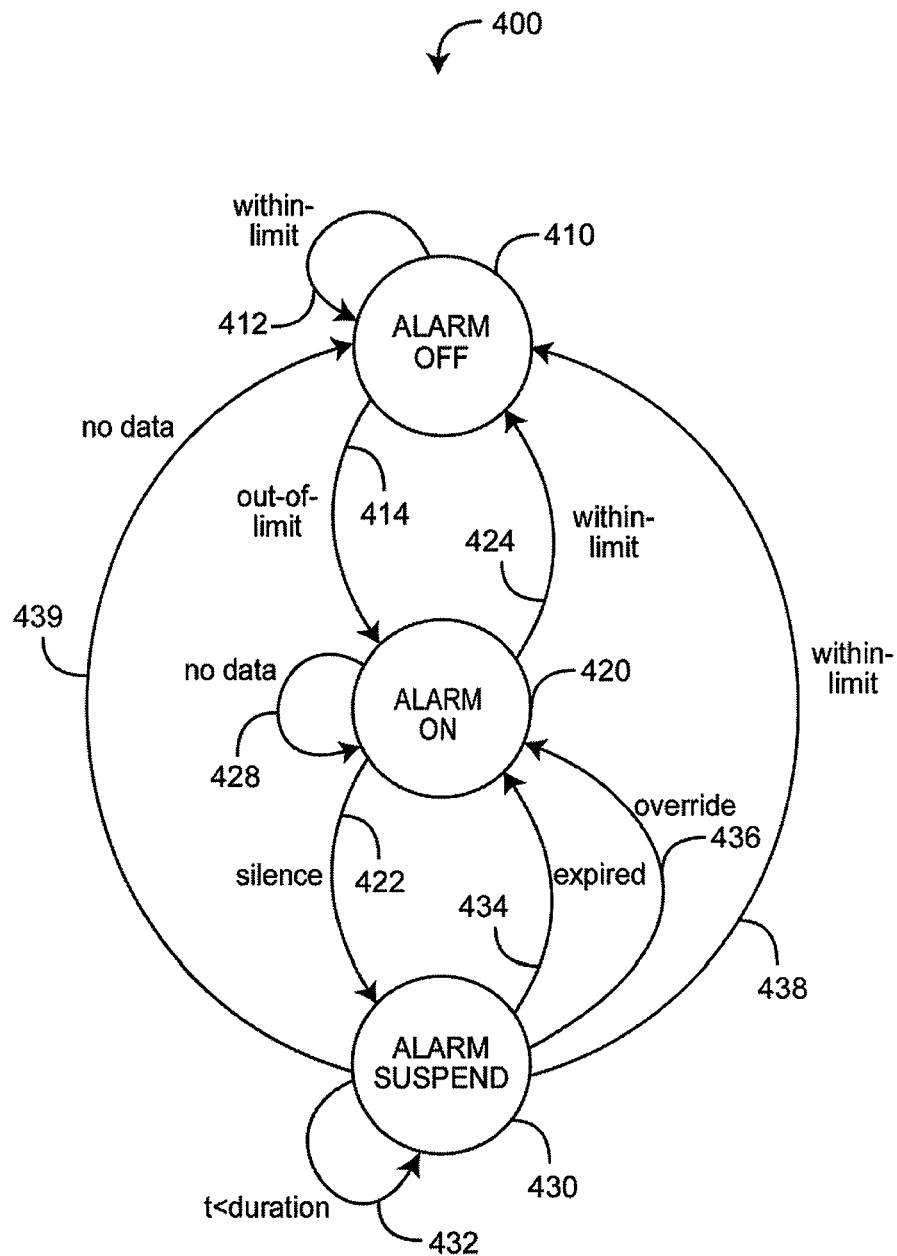
FIG. 4 is a state diagram of an alarm suspend system embodiment.

FIG. 4 illustrates an alarm suspend embodiment 400 that operates independently for each measured parameter that can trigger an alarm. An alarm is initially off 410. The alarm remains off as long as the parameter is within its set limits 412. If a parameter is measured outside of its set limits 414, an alarm is triggered 420. The alarm may audible, visual or both audible and visual. A user can request to silence the alarm by pressing an alarm silence button 144 (FIG. 1), for example. The silence request 422 suspends the alarm 430 which turns off audible alarms but, in an embodiment, does not deactivate visual alarms. The audible alarm remains suspended 430 for a predetermined duration 432. When the suspend duration has passed, the alarm suspend expires 434 and audible alarms are once again activated 420. The alarm remains on 428 until the triggering parameter is within limits 424 or a user once again requests silence 422. The alarm suspend 430 deactivates if the measured parameter becomes within limits 438, such as when the patient condition improves, or if no physiological data is detected 439, such as no sensor, sensor off, no cable or malfunctioning sensor situations, to name a few. Also, if the measured parameter changes during the alarm suspend 430 by a sufficient out-of-limit amount, an override 436 reactivates the audible alarms 420.

In an alarm suspend system embodiment, parameters are classified according to the typical time it takes for medical treatment to transition an out-of-limit measurement to a within-limit measurement. Suspend durations 324 (FIG. 3) are set accordingly. For example, in a two-tier embodiment, relatively slow treatment parameters, such as HbMet, HbCO, Hbt and PVI, are assigned relatively long suspend durations. Similarly, relatively fast treatment parameters, such as $SpO_2$ and PR, are assigned relatively short suspend durations. In an embodiment, the alarm suspend duration is adjustable for each individual parameter, including 2, 5, 10, 15, 20, 25 and 30 minutes for slow treatment parameters, with a default of 15 minutes; and 30, 60, 90 and 120 seconds for fast treatment parameters, with a default of 120 seconds. These alarm features are only active when alarm limits have been set. Other alarm features apply to both slow treatment and fast treatment parameters. For example, an alarm delay of 0, 5, 10 or 15 seconds applies to all enabled parameters.

In an embodiment, an override 436 occurs if slow treatment parameters such as HbCO, HbMet or PVI increase or Hbt decreases by a certain unit change during the alarm suspend duration. The unit change is adjustable for each parameter, such as from 1-15 in increments of 1. TABLE 1 shows a default embodiment of override unit changes for these parameters.

TABLE 1

| Override Unit Changes for Selected Parameters | | |
|---|---|---|
| Parameter | Unit Change | Direction |
| HbCO | 5 | Increase |
| HbMet | 2 | Increase |
| Hbt | 2 | Decrease |
| PVI | OFF | Increase |

Figure 5:
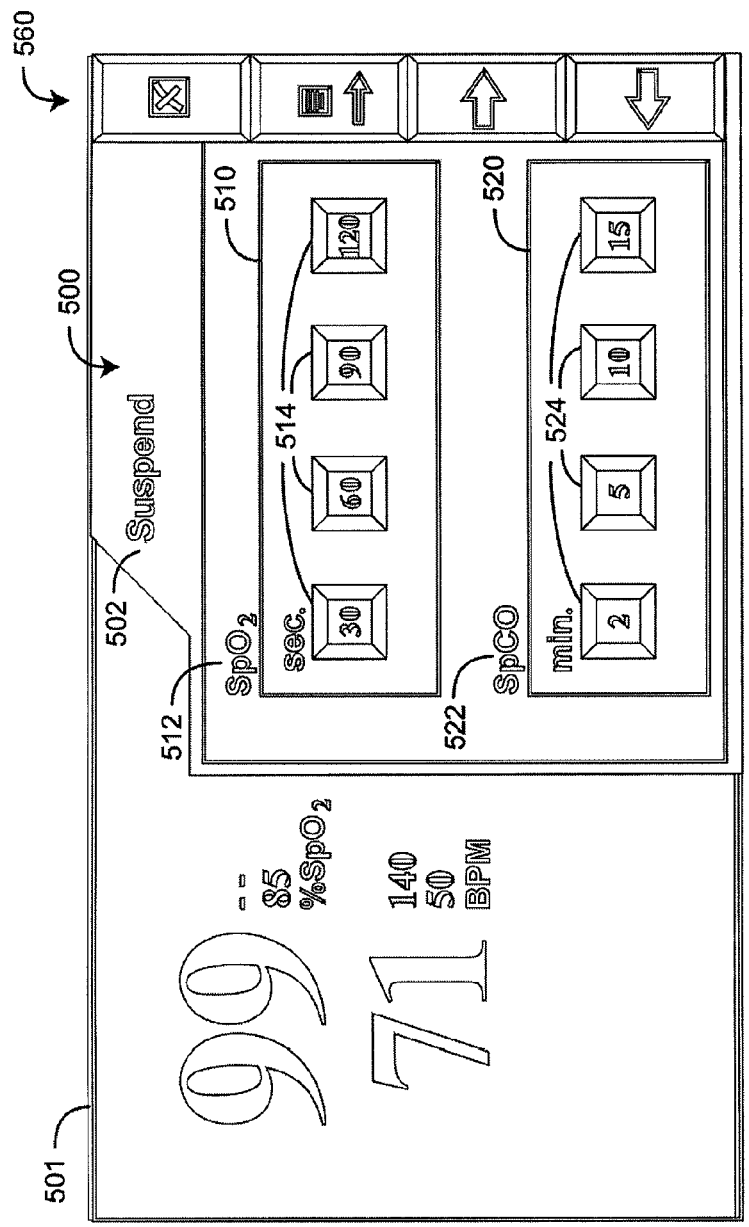
FIG. 5 is an illustration of an alarm suspend pop-up window.

FIG. 5 illustrates an alarm suspend window 500 that provides a "pop-up" display so that a monitor user may manually enter an alarm suspend duration. The alarm suspend window 500 appears as a portion of a monitor display 501, such as the front panel display 120 (FIG. 1) described above. The pop-up window 500 responds to a suspend request, such as a silence button 144 (FIG. 1) press. The alarm suspend window 500 has a window identifier 502 and one or more parameter subsections 510, 520. Each parameter subsection 510, 520 has a parameter identifier 512, 522 and corresponding suspend duration options 514, 524. In an embodiment, specific suspend times are selected via monitor touch keys 130 (FIG. 1) as guided by corresponding touch key icons 560. Selected suspend times are highlighted or otherwise identified and entered, also via a touch key 130 (FIG. 1). In an alternative embodiment, the monitor display is a touch screen and alarm suspend times are directly entered by a finger press on a specific duration "virtual button" 514, 524. Once one or more suspend durations are entered, the pop-up window 500 disappears from the display 501. The alarm suspend window 500 advantageously allows a user to quickly choose an appropriate alarm suspend duration for the situation at hand, rather than relying on a predetermined or default duration.

An alarm suspend system is described above with respect to alarms triggered by measured parameters and limits associated with those measured parameters. Limits may correspond to levels of a measured parameter, such as a percentage oxygen saturation to name but one example. Limits may also correspond to trends of a measured parameter, such as a rate-of-change of oxygen saturation, for example. Limits may also correspond to patterns in a measured parameter or a comparison of one measured parameter with another measured parameter, as further examples.

An alarm suspend system is described above with respect to a two-tier grouping of parameters, such as slow treatment and fast treatment parameters and alarm suspend durations associated with those groups. Groupings of parameters with respect to alarm suspend durations may be multi-tier, such as slow, medium and fast treatment parameters, to name but one example.

An alarm suspend system has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological measurement system comprising:
   a physiological sensor including:
      a plurality of light emitting diodes configured to transmit wavelengths of light onto a tissue site of a patient; and
      at least one detector configured to measure an indication of the wavelengths of light after attenuation by tissue of the patient and output a signal responsive of the attenuated light;
   one or more processors in communication with the physiological sensor, the one or more processors configured to:
      determine a measurement of a physiological parameter based on the signal;
      in response to determining an alarm activation threshold has been satisfied by the physiological parameter measurement, activate an alarm;
      in response to a silence request by a user, suspend the alarm for a parameter-specific period of time; and
      before expiration of the parameter-specific period of time, and in response to determining the physiological parameter measurement no longer satisfies the alarm activation threshold, deactivate the suspended alarm.

2. The physiological measurement system of claim 1, wherein the one or more processors are further configured to:
   determine a second physiological parameter measurement based on the signal;
   in response to determining a second alarm activation threshold has been satisfied by the second physiological parameter measurement, activate a second alarm;
   in response to a second silence request by a user, suspend the second alarm for a second parameter-specific period of time, the second parameter-specific period of time different from the parameter-specific period of time; and
   before expiration of the second parameter-specific period of time, and in response to determining the second physiological parameter measurement no longer satisfies the second alarm activation threshold, deactivate the suspended second alarm.

3. The physiological measurement system of claim 1, wherein the parameter-specific period of time is associated with the physiological parameter.

4. The physiological measurement system of claim 3, wherein the parameter-specific period of time is stored in a memory device in communication with the one or more processors.

5. The physiological measurement system of claim 1, wherein determining the physiological parameter measurement no longer satisfies the alarm activation threshold comprises determining no physiological data is received from the signal.

6. The physiological measurement system of claim 1, wherein determining the physiological parameter measurement no longer satisfies the alarm activation threshold comprises determining a condition of the patient has improved.

7. The physiological measurement system of claim 1, wherein the alarm activation threshold comprises a physiological parameter limit.

8. The physiological measurement system of claim 1, wherein the alarm activation threshold comprises a physiological parameter trend.

9. The physiological measurement system of claim 1, wherein the alarm activation threshold comprises a physiological parameter pattern.

10. An method comprising:
    measuring a physiological parameter using a patient monitoring device, the patient monitoring device including a processor and a memory device configured to store a parameter-specific alarm suspension period of time;
    in response to determining an alarm activation threshold has been satisfied by the physiological parameter measurement, activating an alarm;
    in response to a silence request by a user, suspending the alarm for the parameter-specific alarm suspension period of time; and
    before expiration of the parameter-specific alarm suspension period of time, and in response to determining the physiological parameter measurement no longer satisfies the alarm activation threshold, deactivating the suspended alarm.

11. The method of claim 10, wherein the alarm includes an audible component and a visual component, and wherein suspending the alarm comprises suspending the audible component and not suspending the visual component.

12. The method of claim 10 further comprising:
    measuring a second physiological parameter using the patient monitoring device, the memory device further configured to store a second parameter-specific alarm suspension period of time;
    in response to determining a second alarm activation threshold has been satisfied by the second physiological parameter measurement, activating a second alarm;
    in response to a second silence request by a user, suspending the second alarm for the second parameter-specific alarm suspension period of time; and
    before expiration of the second parameter-specific alarm suspension period of time, and in response to determining the second physiological parameter measurement no longer satisfies the second alarm activation threshold, deactivating the suspended second alarm.

13. The method of claim 10, wherein the parameter-specific alarm suspension period of time is associated with the physiological parameter.

14. The method of claim 10, wherein determining the physiological parameter measurement no longer satisfies the alarm activation threshold comprises determining no physiological data is received from the patient monitoring device.

15. The method of claim 10, wherein determining the physiological parameter measurement no longer satisfies the alarm activation threshold comprises determining a condition of a patient has improved.

16. The method of claim 10, wherein the alarm activation threshold comprises at least one of: a physiological parameter limit, a physiological parameter trend, or a physiological parameter pattern.

17. The method of claim 10, wherein the physiological parameter comprises oxygen saturation.

18. A physiological measurement system comprising:
a physiological sensor means for outputting a signal responsive to a noninvasive measurement of attenuated light transmitted through a tissue site of a patient; and
a processing means in communication with the physiological sensor means and configured to:
  determine a measurement of a physiological parameter based on the signal;
  in response to determining an alarm activation threshold has been satisfied by the physiological parameter measurement, activate an alarm;
  in response to a silence request by a user, suspend the alarm for a parameter-specific period of time; and
  before expiration of the parameter-specific period of time, and in response to determining the physiological parameter measurement no longer satisfies the alarm activation threshold, deactivate the suspended alarm.

19. The physiological measurement system of claim 18, wherein the processing means is further configured to:
  determine a second physiological parameter measurement based on the signal;
  in response to determining a second alarm activation threshold has been satisfied by the second physiological parameter measurement, activate a second alarm;
  in response to a second silence request by a user, suspend the second alarm for a second parameter-specific period of time, the second parameter-specific period of time different from the parameter-specific period of time; and
  before expiration of the second parameter-specific period of time, and in response to determining the second physiological parameter measurement no longer satisfies the second alarm activation threshold, deactivate the suspended second alarm.

20. The physiological measurement system of claim 18, wherein determining the physiological parameter measurement no longer satisfies the alarm activation threshold comprises determining no physiological data is received from the signal.

* * * * *